United States Patent [19]

Blum

[11] 4,230,119
[45] Oct. 28, 1980

[54] MICRO-HEMOSTAT

[75] Inventor: Alvin S. Blum, Fort Lauderdale, Fla.

[73] Assignee: Medical Engineering Corp., Racine, Wis.

[21] Appl. No.: 965,623

[22] Filed: Dec. 1, 1978

[51] Int. Cl.³ .............................................. A61B 17/12
[52] U.S. Cl. ................................ 128/325; 128/334 R; 128/344; 128/349 B
[58] Field of Search .................. 128/334 R, 325, 344, 128/348-351

[56] References Cited

U.S. PATENT DOCUMENTS

| | | | |
|---|---|---|---|
| 2,548,602 | 4/1951 | Greenberg | 128/349 B X |
| 3,050,066 | 8/1962 | Koehn | 128/349 B |
| 3,411,506 | 11/1968 | Velasco | 128/325 |
| 3,516,408 | 6/1970 | Montanti | 128/349 B |
| 3,889,685 | 6/1975 | Miller et al. | 128/348 |
| 3,924,634 | 12/1975 | Taylor et al. | 128/349 B |
| 4,141,364 | 2/1979 | Schultze | 128/344 |
| 4,143,651 | 3/1979 | Patel | 128/349 B |

FOREIGN PATENT DOCUMENTS 574217 10/1977 U.S.S.R. ............................. 128/350 R

OTHER PUBLICATIONS

Mullen et al.-Annals of Thoracic Surg., vol. 23, No. 1, (Jul. 1977), pp. 90-91.

Primary Examiner—Dalton L. Truluck

[57] ABSTRACT

A micro-hemostat especially useful for microsurgery includes a T-shaped member having a highly flexible, double walled tubular bar. The tubular stem of the T-shaped member is connected at one end to the outer wall of the bar and it communicates with an annular space between the walls of the bar. The other end of the stem is connected and communicates with a pressure bulb containing a pressurizing fluid to form a completely closed fluid system. The outer wall of the bar includes cuff portions of highly elastic material adjacent each end of the bar and the inner wall of the bar is a tube of relatively inelastic material. In use, the highly flexible, unpressurized bar is introduced into a blood vessel through an incision using the stem and the pressure bulb as a handle. The bar is then pressurized by squeezing the pressure bulb to inflate the cuff portions to form seals with the inner wall of the blood vessel and to rigidize the normally highly flexible portions of the bar intermediate the cuff portions. As a result blood can flow through the blood vessel only by passing through the lumen of the bar. The stem can be closed to prevent the pressurizing fluid from returning to the pressure bulb and to retain the bar in a pressurized condition until the surgery is completed. A novel method of preparing the micro-hemostat is also disclosed.

6 Claims, 8 Drawing Figures

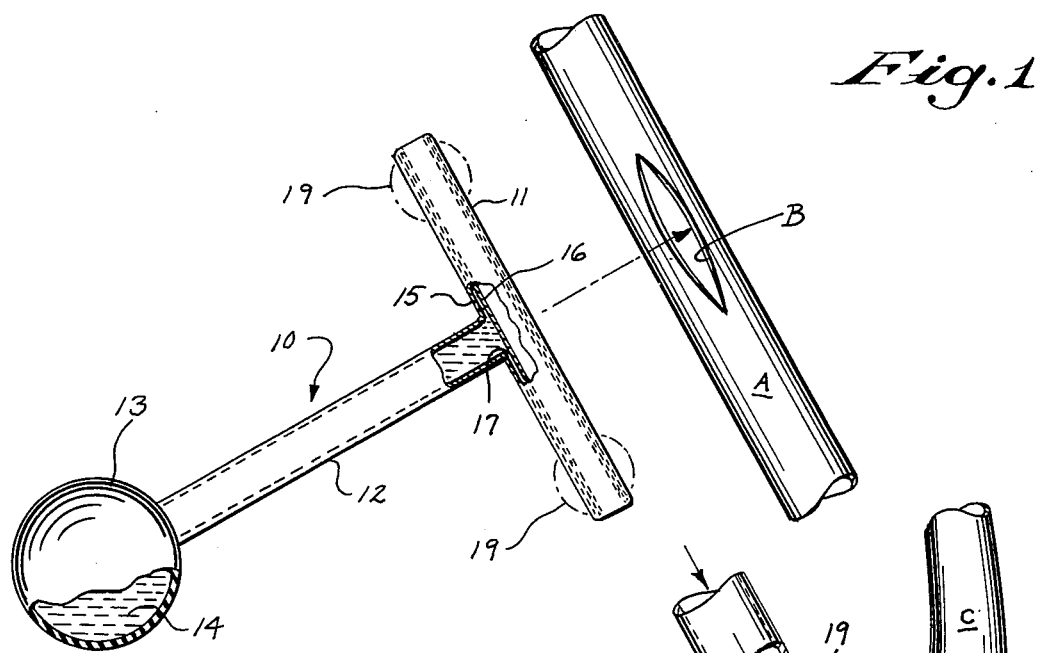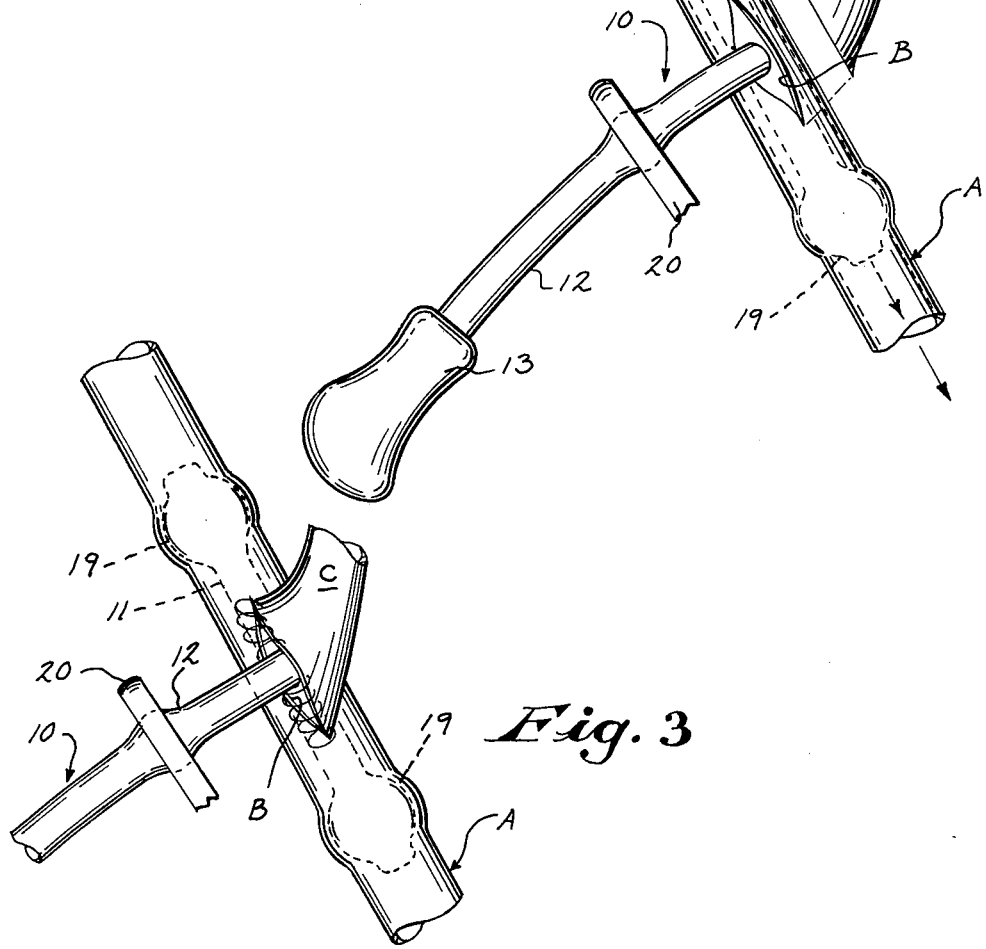

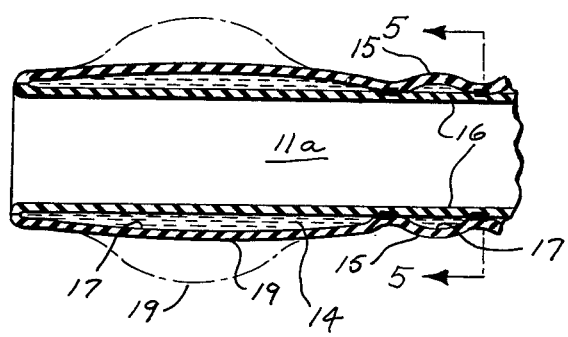
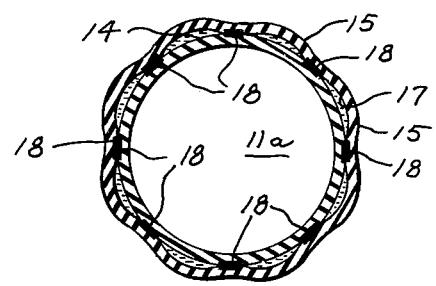
Fig.4　　Fig.5
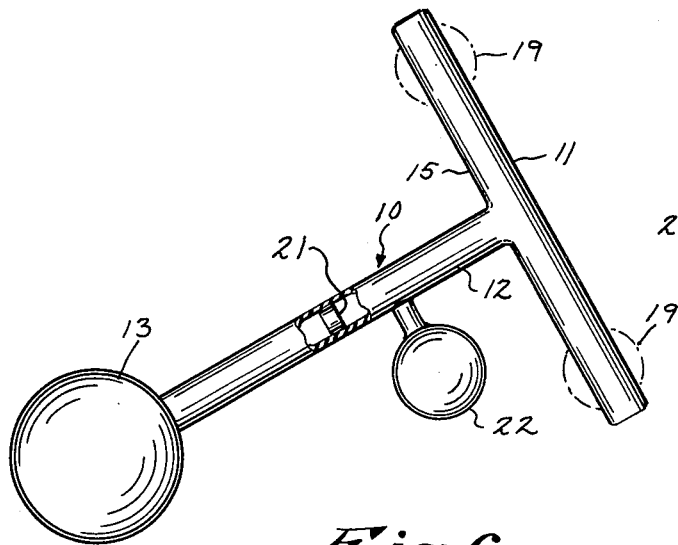
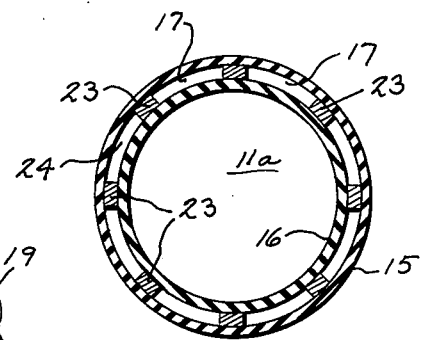
Fig.6　　Fig.8
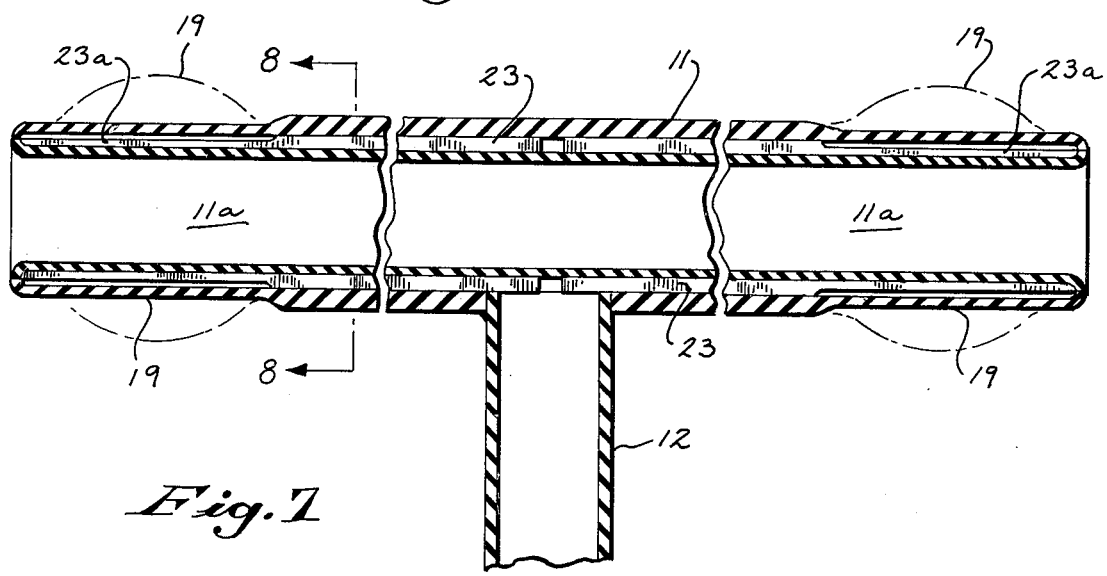
Fig.7

MICRO-HEMOSTAT

The present invention relates generally to the field of surgical equipment and more particularly, to a micro-hemostat for use in vascular surgery.

BACKGROUND OF THE INVENTION

The micro-hemostat of the present invention is particularly useful in anastomosis which is a surgical technique for forming a passage between two normally distinct tubes or vessels of the body.

A common operation in which anastomosis is employed is a coronary artery by-pass operation in which blood is routed about a blocked portion of a coronary artery to restore and insure adequate blood supply to the heart muscle. In the normal by-pass operation, a short segment of a vein taken from another part of the patient's body is used. One end of this vein is connected to the aorta and the other end is connected to the blocked coronary artery below the blockage. The anastomosis connection between the aorta and the artery serves as the by-pass around the blockage.

The standard operative technique for making a coronary artery by-pass comprises first clamping off the aorta to occlude blood flow to all the coronary arteries. The by-pass connection is then made by suturing the veins in place. Many times multiple by-passes are required, and as a result, it may be necessary for the aorta to be clamped off for an extended period of time during which there is no blood supply to the muscle tissue of the heart or the myocardium. The prolonged suspension of blood supply to the heart can result in life threatening infarcts.

Recently a relatively simple technique for the local occlusion of a coronary artery without aortic cross-clamping during anastomosis was described in the literature. Mullen et al, Anals. of Thoracic Surgery, Vol. 23, No. 1 (July, 1977). In the described technique, the flow of blood through the artery is stopped with an occluding device made of silicone rubber and shaped like a T-tube with bulb tips. The occluder is inserted into the artery through an incision and the bulbs occlude the artery bi-directionally during the anastomosis. The occluders are soft and malleable and available in several sizes to fit different sized arteries. The occluder is removed from the artery just prior to placing the final stitches joining the vein and artery.

The occluder and technique described in the Mullen et al article are a significant improvement over the aorta cross-clamping technique previously used. However, there are surgeons who would prefer a technique in which the incision required for insertion and withdrawal of the occluding device would not have to be so large, in which the operating time consumed in selecting the correct size occluder could be reduced and in which the tissue supplied by the artery would not be without circulation while sizing and using the occluder.

SUMMARY OF THE INVENTION

It is an object of the present invention to disclose a micro-hemostat which requires a relatively small incision for insertion and withdrawal, which eliminates the time consumed in selecting the correct size device for an artery and which continues to supply blood to the tissue serviced by the artery during the time required to perform the anastomosis.

It is a further object to disclose a novel method of preparing the micro-hemostat.

The micro-hemostat of the present invention includes a T-shaped member having a highly flexible, double walled tubular bar. The stem of the T-shaped member is connected at one end to the outer wall of the bar and it communicates with an annular space between the walls of the bar. The other end of the stem is connected and communicates with a pressure bulb containing a pressurizing fluid to form a completely closed fluid system. The outer wall of the bar includes cuff portions of highly elastic material adjacent each end of the bar and the inner wall of the bar is a tube of relatively inelastic material. In use, the highly flexible, unpressurized bar is introduced into a blood vessel through an incision using the stem and the pressure bulb as a handle. The bar is then pressurized by squeezing the pressure bulb to inflate the cuff portions to form seals with the inner wall of the blood vessel and to rigidize the normally highly flexible portion of the bar between the cuff portions. As a result blood can flow through the blood vessel only by passing through the lumen of the bar. The stem can be closed to prevent fluid from returning to the pressure bulb and to retain the bar in a pressurized condition until the surgery is completed.

Because of the extremely small size of the micro-hemostat, a novel method of preparing the hemostat had to be developed as conventional assembly techniques proved to be impractical.

In the preferred method of preparation of the micro-hemostat, a T-shaped tube having a bar portion of highly elastic material is first formed and then a flexible, relatively inelastic tube inserted within the lumen of the bar portion of the T-tube. The elastic wall of the bar of the T-shaped tube serves as the outer wall of the double walled bar of the hemostat and the relatively inelastic tube forms the inner wall. The outer and inner walls are sealed at the ends of the bar to form a fluid tight annular chamber. The elastic outer wall of the hemostat bar is then either sealed to the inner wall or coated with a less elastic material to prevent if from expanding or inflating except in the cuff areas adjacent each end of the tube. The stem of the T-shaped tube which communicates with the chamber between the walls, is then connected to a pressure bulb for pressurizing fluid to form a completely closed fluid system. The pressurizing fluid either can be present in the bulb at the time of attachment to the stem of the T-tube or the bulb can be filled with the fluid through a resealable valve after it has been connected to the stem.

The micro-hemostat of the present invention, because of its highly flexible bar with non-preformed bulb ends can be easily folded and bent, thus it requires a smaller incision for insertion and withdrawal than do conventional occluders. Furthermore, since the micro-hemostat is inflatable once in place, a single size hemostat can be used with any of the blood vessels normally encountered in coronary surgery. As a result, the time lost in selecting the proper size occluder is saved. Finally, when the micro-hemostat of the present invention is used, tissue normally supplied by the blood vessel is not without circulation.

In one embodiment, the non-cuff areas of the outer wall are spot sealed with adhesive or welds to the outside of the tube forming the inner wall.

In another embodiment, the outer wall is prevented from inflating or expanding except in the cuff areas by adhesively sealing the inside of the non-cuff portions of the outer wall to ribs on the outside of the tube that forms the inner wall of the bar.

In still another embodiment, the non-cuff areas of the outer wall are coated sufficiently with elastomer to render them relatively inelastic although still highly flexible.

The micro-hemostat and its method of use will be further described in connection with the drawings in the specification which follows.

BRIEF DESCRIPTION OF THE DRAWINGS

FIGS. 1 through 3 are perspective views showing an embodiment of the micro-hemostat of the present invention and its use in a surgical procedure;

FIG. 4 is a cross sectional view of the cuff portion of the bar of the micro-hemostat shown in FIG. 1;

FIG. 5 is a cross sectional view of the bar portion of the micro-hemostat of FIG. 1 taken along lines 5—5 in FIG. 4;

FIG. 6 is a perspective view partly in section of a second embodiment of the micro-hemostat of the present invention;

FIG. 7 is a sectional view of the bar of the micro-hemostat of FIG. 6; and

FIG. 8 is a cross sectional view taken along lines 8—8 of FIG. 7.

In the drawings, the views have been enlarged to facilitate an understanding of the invention.

DESCRIPTION OF THE PREFERRED EMBODIMENT

In the drawings, the micro-hemostat of the present invention is generally referred to as 10, and it is seen to include a generally T-shaped member having a tubular bar 11 and a tubular stem 12 which joins the bar to a pressure bulb 13 containing a pressurizing fluid 14 which is preferably sterile saline. The bar 11 includes an outer wall 15 and an inner wall 16 which are joined in a fluid-tight system at each end of the bar so that the space between the two walls forms an annular chamber 17 for receiving the pressurizing fluid 14. The tubular stem 12 of the hemostat is connected at its inner end to the outer wall 15 of the bar so that the lumen of the stem 12 communicates with the chamber 17. The other end of the stem 12 is connected and communicates with the pressure bulb 13 to form a completely closed fluid system for the pressurizing fluid 14.

In the embodiment of the invention shown in FIGS. 1 through 5, the outer wall 15 is highly elastic, the inner wall 16 is relatively inelastic and the normally annular chamber 17 is deformed by a plurality of spaced seals 18 (seen only in FIGS. 4 and 5). The seals 18 which may be formed with spot welds or adhesives attach the inner wall 16 to the outer wall 15 and are arranged so that all areas of the chamber 17 are interconnected. Thus, when the pressure bulb 13 is squeezed the pressurizing fluid 14 can flow freely to fill the entire chamber 17. The seals 18 are further arranged so that the normally, highly elastic outer wall 15 is prevented from expanding or inflating except for the cuffs 19 adjacent each end of the bar 11 where the inner wall 16 to the outer wall 15 are not attached by seals 18.

The inflated shape of the cuffs 19 is shown by broken lines in FIGS. 1, 3 and 4 and by solid lines in FIG. 2. The pressurizing fluid 14 when introduced into the bar 11 under pressure not only inflates the cuffs 19, but its presence in the intermediate portions of the bar 11 between the cuffs 19 causes the normally flexible bar 11 to become more rigid. As seen in FIGS. 2 and 3, the tubular stem 12 can be closed with an external clamp 20 to retain the pressurizing fluid 14 in the bar so that the cuffs 19 remain inflated and the bar 11 rigid.

In FIG. 6, an embodiment of the micro-hemostat 10 is shown in which there is a one-way valve 21 in the stem 12. The one-way valve 21 prevents the return of the pressurizing fluid 14 to the pressure bulb 13 and eliminates the need to use the external clamp 20 for that purpose. If desired, the valve 21 may be of the type which can be manually opened to permit the return of the fluid 14 to the bulb 13. Suitable valves are disclosed in U.S. Pat. No. 4,009,711 and U.S. Pat. No. 4,060,080.

As seen in FIG. 6, the second embodiment has a safety bulb 22. The safety bulb 22 provides additional assurance that the cuffs 19 will be fully inflated, but not over inflated with pressurizing fluid 14. The wall of the safety tube 22 preferably is made of slightly less elastic material than the elastic wall of the cuffs 19. Thus, when the pressure bulb 13 is squeezed and the pressurizing fluid 14 is forced into the chamber 17 of the bar 11, the cuffs 19 will first expand to form a seal with the blood vessel wall and then when further expansion of the cuffs 19 is restricted, but, before the cuffs 19 can cause damage to the walls of the blood vessel, the safety bulb 22 will expand. Therefore, the user of the second embodiment can visually determine by observing the expanded safety bulb 22 that the cuffs 19 have been sufficiently inflated to form the desired seals with the blood vessel wall. The safety bulb 22 also provides a visual signal when the closed fluid system of the micro-hemostat 10 has been inadvertently opened, e.g., by nicking with a sharp instrument.

In FIGS. 7 and 8, an embodiment of the hemostat 10 is shown in which the tube which serves as inner wall 16 of the bar 11 is provided with longitudinal ribs 23. The ribs 23 cooperate with the walls 15 and 16 to provide channels 24 which permit the pressurizing fluid 14 to flow from the stem 12 through the intermediate arm portions of the bar 11 to the cuffs 19. The presence of the fluid 14 under pressure in the channels 24 renders the flexible bar 11 more rigid. In order to facilitate the flow of pressurizing fluid 14, portions 23a of the ribs 23 are removed in the cuff area and where the stem 12 joins the bar 11.

When a ribbed inner tube is employed as the inner wall 16, it is possible, if desired, to eliminate the use of adhesive or spot welding to prevent the elastic outer wall 15 from expanding. This can be done by coating the non-cuff portions of the outer wall 15 with a material that renders them inelastic. Obviously, the elastic material making up the cuffs 19 must be either protected during the coating process or formed after the coating process is completed.

A preferred method of making the embodiment of the micro-hemostat employing the ribbed tube is to first dip coat a T-shaped mandrel which takes apart for stripping in a silicone elastomer. The mandrel is dipped to form a substantial thickness over the stem 12 and intermediate arm portions of the bar 11 and the silicone material on the mandrel is trimmed off at the two distal ends where the cuffs 19 will start. The mandrel is then dipped again to form an additional layer of cuff thickness and cured. The tips are then trimmed and the material which is to form the cuffs is rolled up back upon itself. The mandrel is removed and a relatively inelastic inner tube with longitudinal ribs 23 is inserted into the lumen of the tubular bar 11 of the thus formed T-tube. The tube preferably has been previously modified by grinding or cutting off segments 23a of the ribs 23 all around the circumference at the center and at the end of each arm in the cuff area to provide the channels 24 for the flow of the pressurizing fluid. If desired, the tops of the ribs on the tube can then be coated with adhesive before the tube is positioned inside the bar of the T-tube. Using an inflatable mandrel the adhesive coated ribs 23 of the inner tube can be forced against the inner wall of the bar of the T-tube. A tapered mandrel can also be used for the same purpose. When the adhesive is cured, the cuffs can be unrolled and the ends of the outer wall 15 and inner wall 16 sealed by dip coating or cementing. Finally, the pressure bulb 13 can be attached to the stem 12 with adhesive to form the complete micro-hemostat 10.

The pressure bulb is preferably provided with a resealable valve so that it can be filled after it has been thus assembled. A suitable resealable valve which is also comprised of silicone material is disclosed in U.S. Pat. No. 3,919,724.

Although in the preferred embodiments of the invention which have been described, the entire micro-hemostat has been described as being made of medical grade silicone, other suitable materials such as polyurethane also can be used.

In the embodiments of the invention shown in the drawings, the pressurized bar of the micro-hemostat can be depressurized by either unclamping the stem, opening the one-way valve or cutting the stem. Since the prepared pressurizing fluid is sterile saline there is no disadvantage in cutting the stem and cutting the stem does have its advantage that the hemostat will not be reused.

A method of using the micro-hemostat 10 will now be described in connection with FIGS. 1, 2 and 3. Prior to using the micro-hemostat 10 a section of artery A to be anastomosed is located and a longitudinal incision B is made. The unpressurized, highly flexible bar 11 of the micro-hemostat is then easily inserted into the artery A through the incision B using the bulb 13 and stem 12 as the handle. The bar 11 is positioned in the blood vessel A so that the ends of the bar 11 extend in opposite directions from stem 12 past the edges of the incision B. Since the hemostat 10 is inserted downstream of the blockage in the artery A, the insertion is normally accomplished without any great loss of blood. The pressure bulb 13 is squeezed to force the pressurizing fluid 14 into the chamber 17 to inflate the cuffs 19 and rigidize the intermediate arm portions of the bar 11. When the cuffs 19 have been adequately inflated, the blood flowing through the artery passes through the lumen 11a of the tubular bar 11. When the hemostat 10 is properly in place and pressurized the stem 12 is then closed with either a one-way valve 21 or an external clamp 20 as seen in FIG. 3 to keep the bar 11 pressurized and the cuffs 19 inflated.

The blood vessel C to be connected to artery A is then placed over the incision B as seen in FIG. 3. Artery A is then lifted from inside by using the stem 12 and bulb 13 as a handle to stabilize the artery and facilitate the suturing of the blood vessel C to the artery about the incision B. Sutures are prepared about the incision through which the stem 12 extends, but are not drawn tight. The clamp 20 is then removed to permit the pressurizing fluid to leave the cuffs and the intermediate portion of the bar 11 and to return to the pressure bulb 13 so that the micro-hemostat 10 can be readily removed from the artery A. Once again, the stem 12 and the pressure bulb 13 are used as a handle for this purpose. The suturing of the blood vessel C to the artery A is then quickly completed with a minimum of blood loss. Because of the flexibility and softness of silicone rubber the use of the preferred micro-hemostat results in a minimum of trauma to the site of the anastomosis.

It will be readily apparent to those skilled in the art, that a number of modifications and changes can be made without departing from the spirit and scope of the present invention. For example, in some instances it may be desirable to replace the pressure bulb of the described micro-hemostat with a resealable cap on the stem. The pressurizing fluid to rigidize the highly flexible bar and inflate the cuff is then introduced under pressure from a separate bulb or syringe through a cannula extending through the resealable cap; the opening in the cap formed by the cannula closes upon the withdrawal of the cannula. Other conventional means of closing the stem may also be employed. Therefore, it is intended that the invention not be limited except by the claims which follow.

I claim:

1. A micro-hemostat useful in micro-surgery during anastomosis of blood vessels comprising
   (a) a highly flexible tubular bar having a flexible, relatively inelastic inner wall and a flexible elastic outer wall, said walls being joined together at the ends of the bar to form an annular chamber defined by the space between the walls, said inner wall forming a passage through which uninterrupted blood flow takes place when the tubular bar is placed within a blood vessel;
   (b) means preventing said outer wall from expanding when the chamber is pressurized except for areas adjacent each end of the bar which can be inflated under pressure to form annular cuffs; and
   (c) a tubular stem attached at one end to the outer wall of said bar between said cuff areas at a point intermediate the length of the bar permitting said chamber to be pressurized therethrough, said stem having a passage therethrough which communicates with the annular chamber.

2. A micro-hemostat of claim 1 in which the means preventing the outer wall from expanding are spot seals which join the outer wall to the inner wall without preventing flow through the annular chamber.

3. A micro-hemostat of claim 1 which includes a pressure bulb for pressurizing fluid, said bulb being connected to the other end of the stem to form a closed fluid system whereby pressurizing fluid in the pressure bulb can be transferred from the pressure bulb through the passage in the stem to the annular chamber to inflate the areas which form cuffs and to render the flexible bar more rigid.

4. A micro-hemostat of claim 3 in which the pressure bulb contains sterile saline.

5. A micro-hemostat of claim 4 in which the stem is provided with a one-way valve permitting the flow of fluid from the pressure bulb to the arm.

6. A micro-hemostat of claim 1 in which the inner wall of the bar has external, longitudinal ribs.

* * * * *